US008460185B2

(12) United States Patent
Epstein et al.

(10) Patent No.: US 8,460,185 B2
(45) Date of Patent: Jun. 11, 2013

(54) ARTICULATED SURGICAL RETRACTOR

(76) Inventors: Stephen T. Epstein, Newtown, PA (US); Andre Martens, Linter (BE); Hugo Karel I. Vanermen, Knokke-Heist (BE); John Sinisi, Warminster, PA (US)

( * ) Notice: Subject to any disclaimer, the term of this patent is extended or adjusted under 35 U.S.C. 154(b) by 542 days.

(21) Appl. No.: 12/541,160

(22) Filed: Aug. 14, 2009

(65) Prior Publication Data

US 2009/0299147 A1 Dec. 3, 2009

Related U.S. Application Data

(63) Continuation-in-part of application No. PCT/EP2007/051466, filed on Feb. 15, 2007.

(51) Int. Cl.
*A61B 1/32* (2006.01)

(52) U.S. Cl.
USPC .......... 600/213

(58) Field of Classification Search
USPC .......... 600/201–246
See application file for complete search history.

(56) References Cited

U.S. PATENT DOCUMENTS

2004/0143163 A1 * 7/2004 Palmer et al. .......... 600/204

* cited by examiner

*Primary Examiner* — Andrew Yang
*Assistant Examiner* — Diana S Jones
(74) *Attorney, Agent, or Firm* — LaMorte & Associates, P.C.

(57) ABSTRACT

A surgical retractor assembly that utilizes a tubular shaft and a connection nub. A pivot joint connects one end of the tubular shaft to the connection nub. The pivot joint enables the connection nub to move relative the tubular shaft along a path that is coplanar to the axis of the tubular shaft. Together, the tubular shaft and the connection nub create an elongated element that can be introduced into a small incision. A retractor blade is provided. A bearing joint extends from the retractor blade. The retractor blade and bearing joint are introduced into a surgical site independent of the elongated element. Within the surgical site, the connection nub interconnects with the bearing joint, therein joining the retractor blade to the tubular shaft and a handle.

13 Claims, 5 Drawing Sheets

10 12 14 16 18 20 22 24 26 28 30 32 34 36 44

34
32
44
26
36
24
22
20
30
18
10
16
12
28
14

46
50
52
28

ARTICULATED SURGICAL RETRACTOR

RELATED APPLICATIONS

This application is a continuation-in-part of PCT/EP2007/051466, filed Feb. 15, 2007, and entitled Improved Atrial Retractor.

BACKGROUND OF THE INVENTION

1. Field of the Invention

In general, the present invention relates to single blade retractors that are used during surgical procedures. More particularly, the present invention relates to surgical retractors having a blade that can be selectively adjusted in orientation to meet the needs of a surgeon.

2. Prior Art Description

Surgical retractors are used to move tissue during surgery. Generally, retractors are either single bladed or double bladed. A double bladed retractor has two blades that either separate tissue or compress tissue as the blades are moved toward or away from each other. Such retractors are most often used to spread tissue or bone apart during a surgical procedure so that there is room for the surgeon to operate. Single blade retractors have only a single blade. The blade is typically static and is positioned at a right angle to the handle of the retractor in the same manner as the blade on a garden hoe. Single blade retractors are typically used by a surgeon during an invasive surgery to selectively manipulate tissue within the body during the course of the surgery.

A problem associates with most single blade retractors is that they are large cumbersome instruments. As such, they are typically only used during invasive surgical procedures. However, in modern surgery, invasive surgical procedures are becoming less common. Rather, many traditionally invasive surgical procedures are being replaced with minimally invasive surgical procedures. In a minimally invasive surgical procedure, very small incisions are made into the body. Long instruments are then inserted into the small incisions to access the area within the body cavity needing surgery. The small incisions cause much less injury to the body than does an invasive surgical procedure. Accordingly, the patient typically recovers more rapidly from the surgery with less adverse side effects.

During some surgical procedures, such as heart valve surgery, a retractor is needed to manipulate the heart muscle so that unobstructed access is provided to the surgical site. However, if the surgery is minimally invasive, traditional retractors cannot be brought into the surgery site. The surgeon is therefore limited to small retractors at the ends of probes that can be inserted through the small surgical incisions. These retractors are typically inadequate in size. Furthermore, the room available to manipulate the retractor is severely limited by the surgical incision. As a result, the small retractor cannot always be manipulated into a position where it is of the most use to the surgeon.

A need therefore exists for a retractor having a large blade that can be used in a minimally invasive surgical procedure, wherein the orientation of the blade can be selectively adjusted without having to reorient the entire retractor. This need is met by the present invention as described and claimed below.

SUMMARY OF THE INVENTION

The present invention is a retractor assembly for use during a minimally invasive surgical procedure. The retractor assembly utilizes a tubular shaft having a first end and a second end. The tubular shaft extends along an imaginary shaft axis. The retractor assembly also utilizes a connection nub. A pivot joint connects the second end of the tubular shaft to the connection nub. The pivot joint enables the connection nub to move relative the tubular shaft only along a path that is coplanar to the axis of the tubular shaft. Together, the tubular shaft and the connection nub create an elongated element that can readily be introduced into a surgical site using only a small incision.

A retractor blade is provided. A bearing joint extends from the retractor blade. The retractor blade and bearing joint are introduced into a surgical site independent of the elongated element. Within the surgical site, the connection nub interconnects with the bearing joint, therein joining the retractor blade to the tubular shaft and handle. The bearing joint rotates about a single axis of rotation, wherein the axis of rotation is coplanar with the axis of the tubular shaft.

Once at the surgical site, the position of the retractor blade can be selectively adjusted to meet the needs of a surgeon.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Although the present invention retractor can be embodied in different ways for different surgical procedures, the embodiment illustrated shows the retractor configured for use during surgery of the arterial valve within the heart. This embodiment is selected in order to set forth the best mode contemplated for the invention. The illustrated embodiment, however, is merely exemplary and should not be considered a limitation when interpreting the scope of the appended claims.

Figure 1:
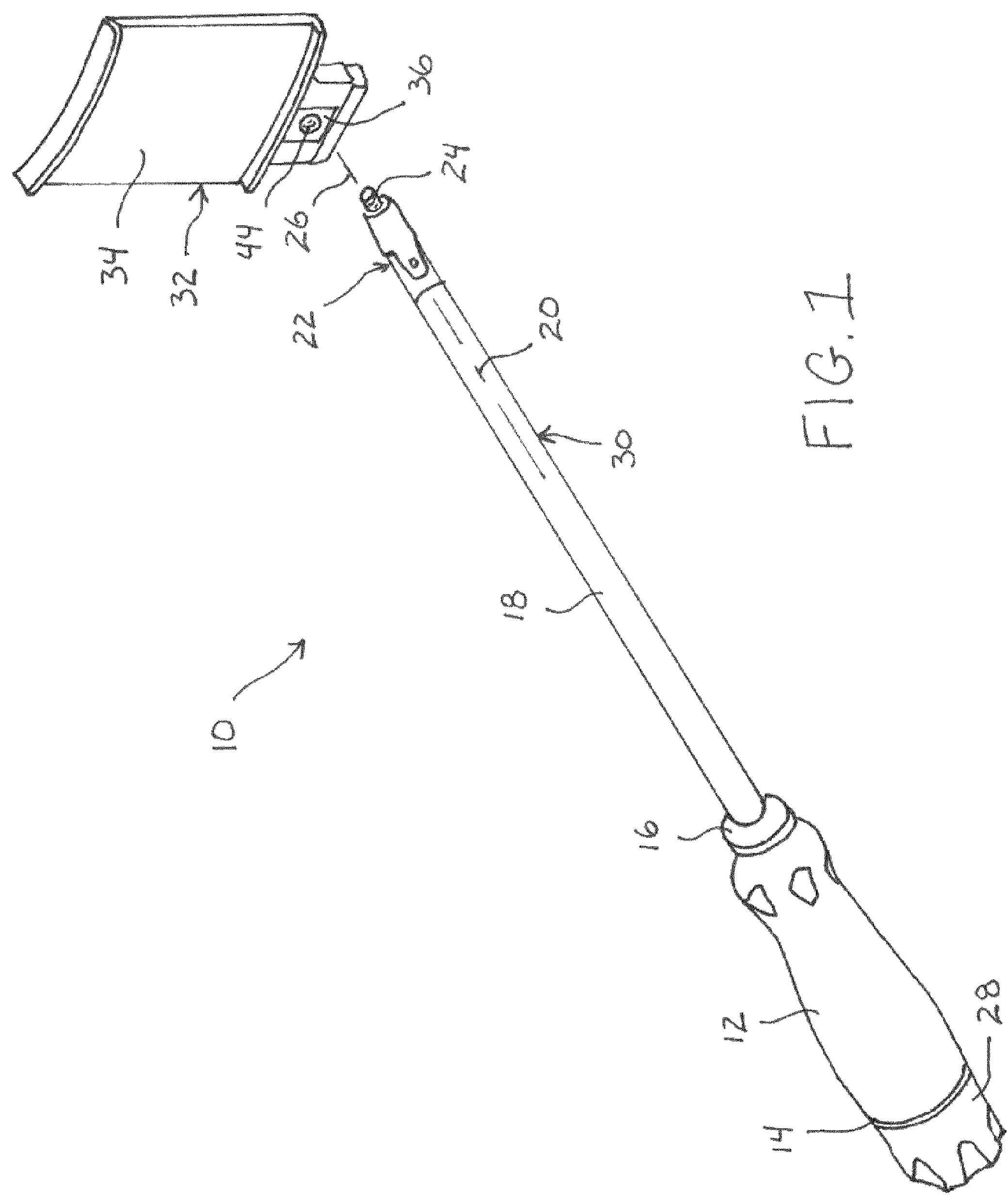
FIG. 1 is a perspective view of an exemplary embodiment of a retractor assembly.
Figure 2:
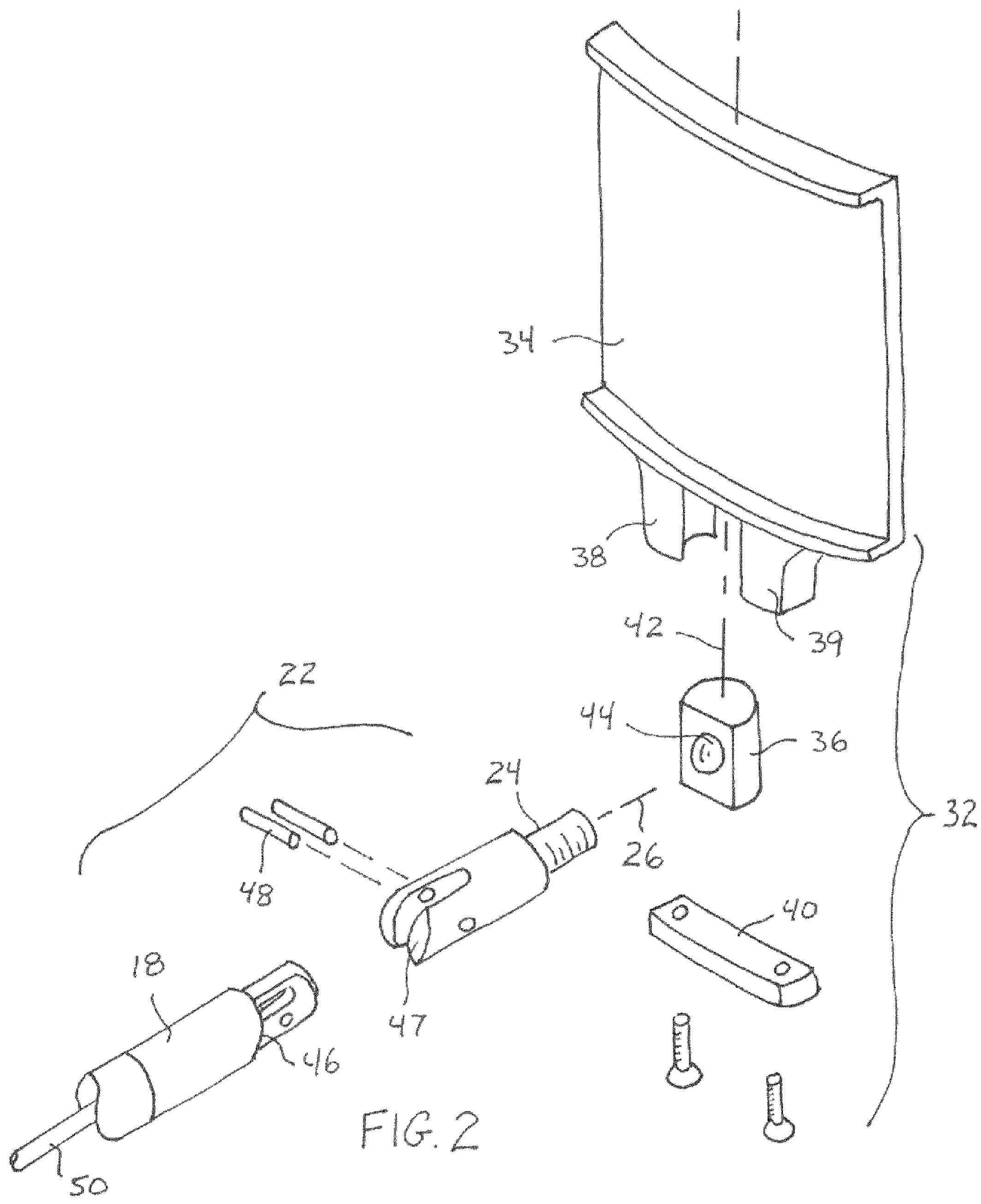
FIG. 2 is an exploded perspective view of a distal end of the exemplary retractor assembly.

Referring to FIG. 1 and FIG. 2, a retractor assembly 10 is shown. The retractor assembly 10 has a handle 12 with a first end 14 and an opposite second end 16. A tubular shaft 18 extends from the second end 16 of the handle 12. The tubular shaft 18 extends straight along an imaginary longitudinal shaft axis 20. The tubular shaft 18 terminates with a hinge joint 22.

The hinge joint 22 joins a connection nub 24 to the tubular shaft 18. The connection nub 24 extends along an imaginary nub axis 26. The hinge joint 22 enables the connection nub 24 to rotate through a range about the hinge joint 22 in a plane that is coplanar with the longitudinal shaft axis 20 of the tubular shaft 18. As such, it will be understood that the hinge joint 22 enables the connection nub 24 to move in only a single plane so that the nub axis 26 of the connection nub 24 and the longitudinal shaft axis 20 of the tubular shaft 18 are always in a common plane. The connection nub 24 can be brought into linear alignment with the tubular shaft 18. However, it can also be angled either upwardly or downwardly relative the longitudinal shaft axis 20 of the tubular shaft 18.

An adjustment knob 28 is positioned at the first end 14 of the handle 12. As will later be explained in detail, the movement of the connection nub 24 is selectively controlled by the manual turning of the adjustment knob 28. It will therefore be understood that the connection nub 24 can be brought into linear alignment with the tubular shaft 18. The tubular shaft 18 and connection nub 24 can then be inserted into a body cavity through a small incision. Once within the body cavity, the orientation of the connection nub 24 can be selectively changed by turning the adjustment knob 28 on the handle 12.

The tubular shaft 18 and the connection nub 24 form an elongated element 30 that can be manually manipulated via the handle 12. The elongated element 30 can be introduced into most surgical sites using traditional minimally invasive incisions. The connection nub 24 at the end of the elongated element 30 engages a blade assembly 32. The blade assembly 32 consists of a retractor blade 34 and a semi-cylindrical bearing 36 that is mounted to one edge of the retractor blade 34. The semi-cylindrical bearing 36 is held within confinement arms 38, 39 and is prevented from exiting the confinement arms 38, 39 by an end cap 40. The shape of the semi-cylindrical bearing 36 and the confinement arms 38, 39 enable the semi-cylindrical bearing 36 to move about an imaginary axis of rotation 42 relative the retractor blade 34.

A receptacle 44 is disposed within the semi-cylindrical bearing 36. The receptacle 44 is sized to receive and engage the connection nub 24. In the exemplary embodiment being illustrated, both the receptacle 44 and the connection nub 24 are threaded. This is one possible connection type. When the connection nub 24 is tightened into the receptacle 44, the nub axis 26 aligns at a perpendicular to the axis of rotation 42 for the semi-cylindrical bearing 36. Accordingly, it will be understood that once the connection nub 24 is received into the receptacle 44, the axis or rotation 42 for the semi-cylindrical bearing 36 is maintained in the same plane as both the nub axis 26 and the longitudinal shaft axis 20 of the tubular shaft 18.

Figure 3:
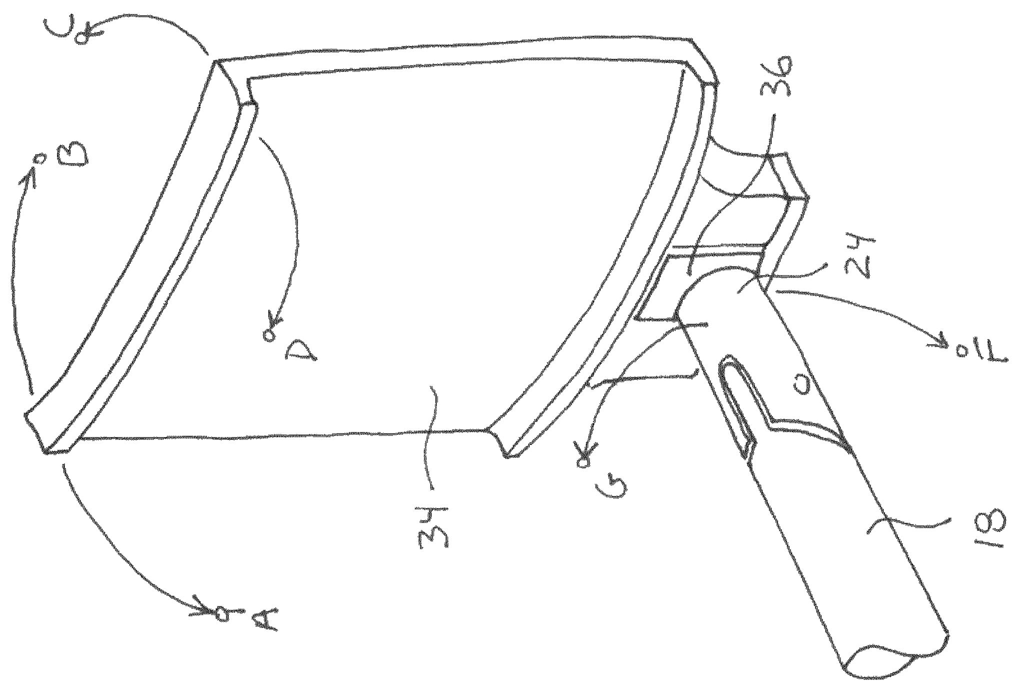
FIG. 3 is an assembled view of that shown in FIG. 2, showing marked ranges of motion.

Referring to FIG. 3 in conjunction with FIG. 2, the full range of motion for the retractor blade 34 can now be understood. Once the connection nub 24 is attached to the semi-cylindrical bearing 36, the retractor blade 34 becomes interconnected with both the tubular shaft 18 and the handle 12 (FIG. 1). The retractor blade 34 is capable of rotating about the axis of rotation 42 of the semi-cylindrical bearing 36. This enables the retractor blade 34 to move between points A, B, C, D as illustrated. In addition, the entire blade assembly 32 can be raised or lowered in relation to the tubular shaft 18 by changing the orientation of the connection nub 24 and the tubular shaft 18 at the hinge joint 22. The connection nub 24 can be moved between points E and F, as illustrated. However, throughout all possible movements, the axis of rotation 42 for the semi-cylindrical bearing 36, the nub axis 26 and the longitudinal shaft axis 20 of the tubular shaft 18 remain coplanar.

Figure 4:
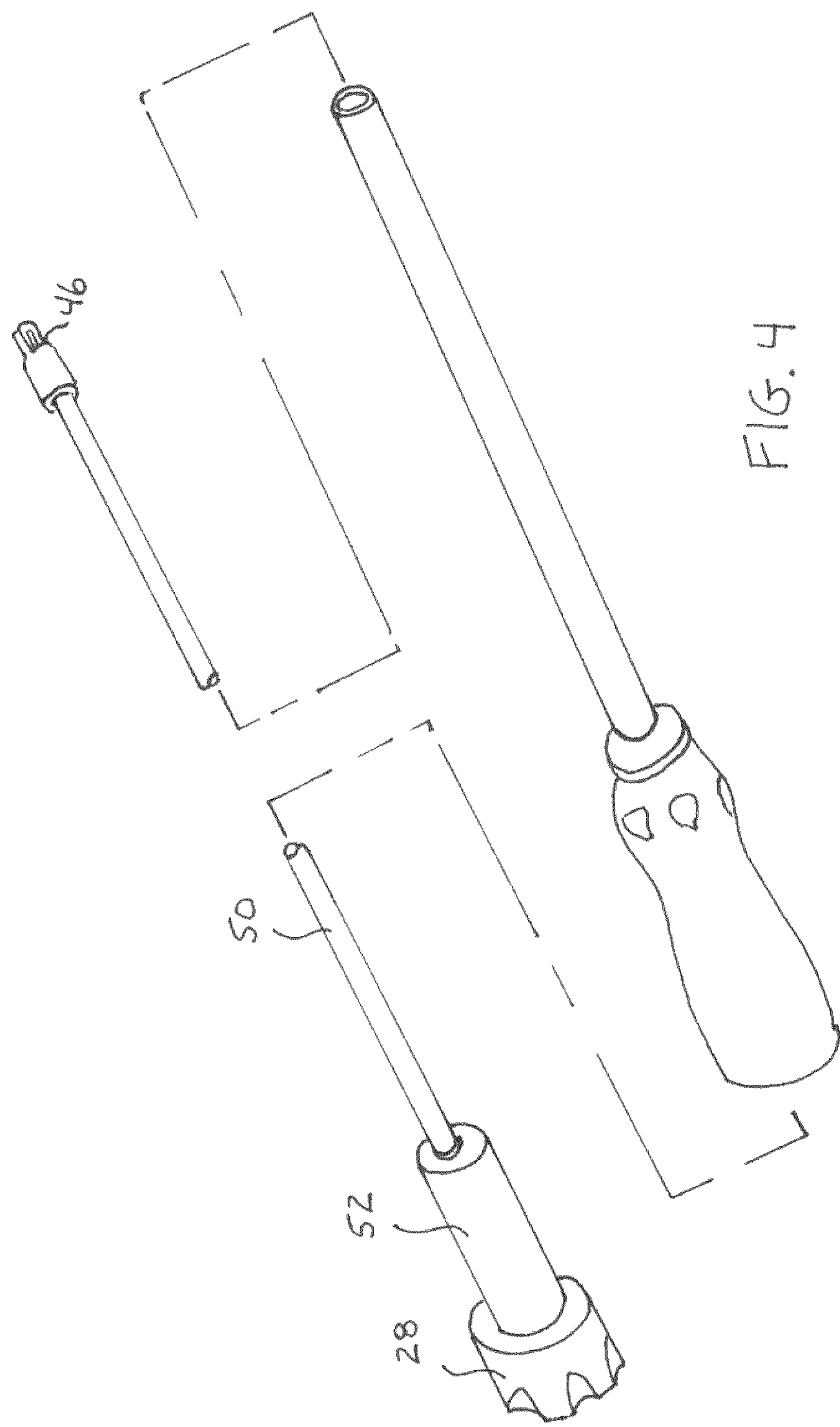
FIG. 4 is a partially exploded view of the proximal end of the exemplary retractor assembly.

Referring to FIG. 2 in conjunction with FIG. 4, it can be seen that the tubular shaft 18 and the connection nub 24 have cam surfaces 46, 47 that interconnect to form the hinge joint 22. The shaped cam surfaces 46, 47 are maintained in abutment by an offset pivot pin 48 that joins the tubular shaft 18 to the connection nub 24. The tubular shaft 18 is hollow between the handle 12 and the hinge joint 22. A slide rod 50 is disposed within the tubular shaft 18. The slide rod 50 extends into the hinge joint 22 and engages the connection nub 24. When tension is applied to the slide rod 50, the cam surface 47 of the connection nub 24 are pulled against the cam surface 46 of the tubular shaft 18 and consequently the hinge joint 22 is caused to bend in one direction. When an opposite compression force is applied to the slide rod 50, the cam surfaces 46, 47 move in the opposite direction and the hinge joint 22 bends in the opposite direction. The shape of the cam surfaces 46, 47 depends upon the degree of movement desired. In a preferred embodiment, the hinge joint 22 is capable of being moved through a range of at least thirty degrees. The hinge joint 22 illustrated is merely exemplary of a mechanically adjustable joint. The full operation of the illustrated embodiment is described in co-pending PCT patent application No. PCT/EP2007/051466, the description of which is incorporated into this specification by reference.

The slide rod 50 is attached to an adjustment mechanism 52. The adjustment mechanism 52 is maintained mostly inside the handle 12. The adjustment mechanism 52 is controlled by the adjustment knob 28. When the adjustment knob 28 is turned in one direction, it extends the slide rod 50 in one direction. Conversely, when the adjustment knob 28 is turned in the opposite direction, the slide rod 50 retreats. There are a great many adjustment mechanisms that can turn the rotational movement of a knob into the linear movement of a shaft. Any such adjustment mechanism can be adapted for use as part of the present invention.

Returning to FIG. 1, it will be understood that to use the present invention retractor assembly 10, a first incision is made in a body cavity. The blade assembly 32 is then inserted into the body cavity through that incision using any appropriately sized set of forceps. The blade assembly 32 has a narrow cross section. As such, only a narrow incision needs to be made and the blade assembly 32 can be advanced through that incision with minimal disruption to surrounding tissue.

Once the blade assembly 32 is in place, another small incision is made into the body cavity. The tubular shaft 18 and connection nub 24 are then advanced through that second incision. Once in the body cavity, the connection nub 24 is tightened into the threaded receptacle 44 in the blade assembly 32. This interconnects the blade assembly 32 with the tubular shaft 18 and handle 12. Utilizing the adjustment knob 28 on the handle 12, the orientation of the blade assembly 32 can then be altered to the needs of the surgeon.

The technique of separately inserting the blade assembly 32 into a body cavity enables the surgeon to use much smaller incisions that would otherwise be necessary if the retractor assembly were a single piece. Furthermore, by inserting the tubular shaft 18 through a separate incision, the positioning of the retractor assembly 10 can be customized to the needs of a surgeon and the handle 12 of the retractor assembly 10 can be oriented in places not possible for traditional one-piece retractors.

Figure 5:
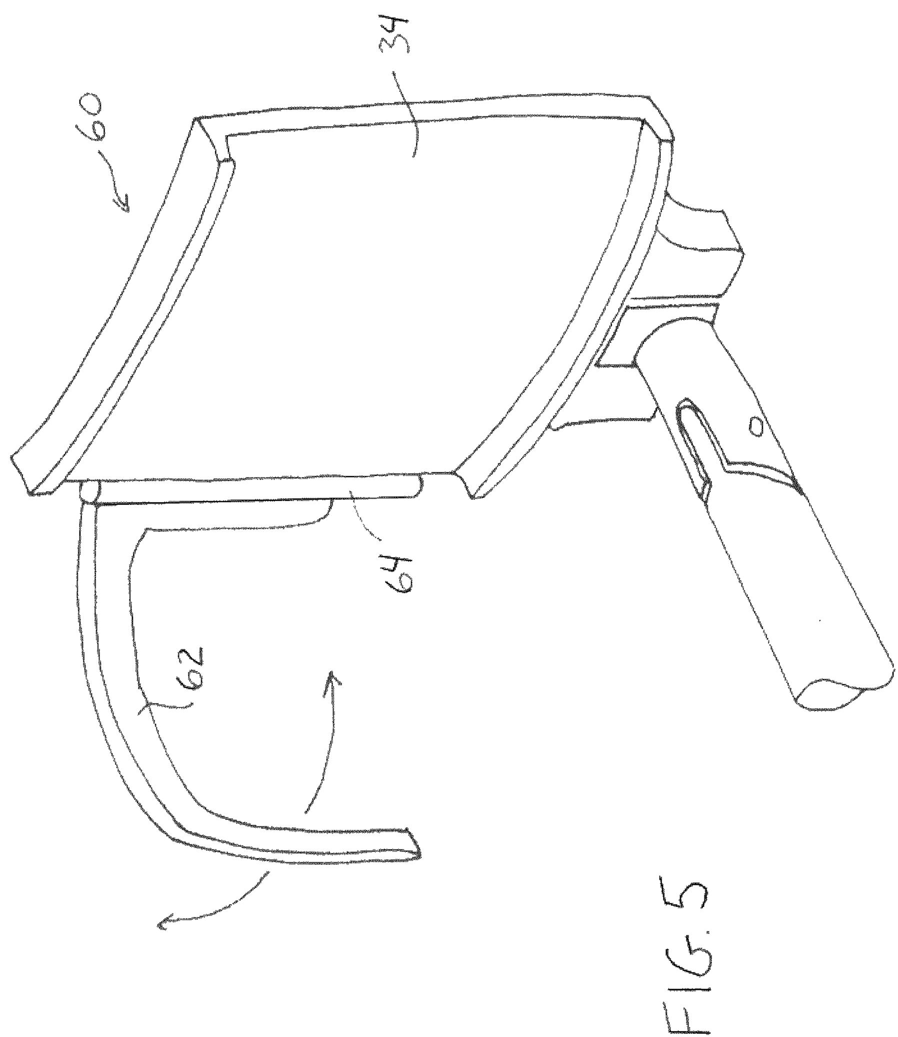
FIG. 5 is an exploded perspective view of an alternate configuration of a retractor blade assembly.

Referring now to FIG. 5, an alternate embodiment of a blade assembly 60 is shown. The alternate embodiment shows many of the features previously described. As such, the same reference numbers will be maintained in order to avoid confusion. The blade assembly 60 connects to a tubular shaft and handle in the same manner as the original embodiment. What differentiates this alternate embodiment is the addition of a secondary flap 62 to the side of the retractor blade 34.

The flap 62 is attached to an edge of the retractor blade 34 with a hinge connection 64. The hinge connection 64 enables the flap 62 to be either extended away from the retractor blade 34 or folded against the retractor blade 34. By folding the flap 62 against the retractor blade 34, the overall blade assembly 60 can still be inserted into a body cavity through a narrow incision. However, once in the body cavity, the flap 62 can be unfolded, therein greatly increasing the effective size of the retractor.

The flap 62 can be solid (not shown) or complex in shape (shown). As such, different flaps can be created for different surgical needs. The use of a complex flap 62 may be desirable if a solid flap would impair a surgeon's line of site during an operation.

It will be understood that the embodiments of the present invention that are illustrated and described are merely exemplary and that a person skilled in the art can make many variations to those embodiments. For instance, in the exemplary embodiment, the connection nub engages the blade assembly using a screw thread connection. This interconnection is one of many possible connection types. Bayonet couplings, locking finger connections, snap-fit connection, and friction fit connections are just a few of the connection types that can be used in place of the illustrated threaded connection. Likewise, it should be understood that the shape of the blade panel and/or flap can be altered to the needs of a particular surgeon. Furthermore, the length of the tubular shaft and connection nub can be altered to the needs of a surgeon. All such embodiments are intended to be included within the scope of the present invention as defined by the claims.

What is claimed is:

1. A retractor assembly that is adjustable through a range of motion, said retractor assembly comprising:
- a tubular shaft having a first end and a second end, wherein said tubular shaft extends along an imaginary shaft axis;
- a connection nub having a first end and a second end, wherein said connection nub extends along a nub axis;
- a pivot joint connecting said second end of said tubular shaft to said first end of said connection nub, wherein said pivot joint enables said connection nub to move relative said tubular shaft; and
- a retractor blade coupled to said second end of said connection nub with a bearing joint, wherein said bearing joint rotates about a single axis of rotation relative said retractor blade, wherein said single axis of rotation is perpendicular to said nub axis, and wherein said single axis of rotation, said nub axis, and said imaginary shaft axis are coplanar throughout said range of motion.

2. The assembly according to claim 1, wherein said retractor blade is selectively detachable from and attachable to said connection nub.

3. The assembly according to claim 1, further including a handle coupled to said first end of said tubular shaft.

4. The assembly according to claim 3, further including a mechanical adjustment mechanism for causing said connection nub to move relative said tubular shaft.

5. The assembly according to claim 4, wherein said mechanical adjustment mechanism has a control knob supported by said handle.

6. The assembly according to claim 4, wherein said mechanical adjustment mechanism includes a tensioning rod that extends through said tubular shaft and engages said connection nub across said pivot joint.

7. The assembly according to claim 1, further including at least one flap coupled to said retractor blade by a hinge connection.

8. A retractor assembly, comprising:
- a handle;
- an elongated element extending from said handle, said elongated element having an tubular shaft and a connector nub joined together at a pivot joint, wherein said tubular shaft extends along a shaft axis and said connector nub extends along a nub axis, and said pivot joint enables said shaft axis and said nub axis to selectively orient at a range of angles;
- a retractor blade;
- a bearing joint interposed between said retractor blade and said elongated element, said bearing joint being rotatable only about a single axis of rotation relative said retractor blade, therein enabling said retractor blade to be altered in orientation relative said elongated element, wherein said single axis of rotation is perpendicular to said nub axis; and wherein said single axis of rotation, said nub axis, and said shaft axis are always coplanar; and
- wherein said elongated element is selectively attachable to and detachable from said bearing joint.

9. The assembly according to claim 8, further including an adjustment mechanism for selectively creating a bend in said pivot joint.

10. The assembly according to claim 8, wherein said elongated element interconnects with said bearing joint with a threaded connection.

11. The assembly according to claim 8, further including at least one flap coupled to said retractor blade by a hinge connection.

12. A retractor assembly, comprising:
- an elongated element having an tubular shaft and a connector nub joined together at a pivot joint, wherein said tubular shaft extends along a shaft axis and said connector nub extends along a nub axis;
- a retractor blade;
- a bearing interposed between said retractor blade and said elongated element that rotates about a single axis of rotation that is perpendicular to said nub axis, wherein said single axis of rotation, said nub axis, and said shaft axis are always coplanar, and wherein said bearing forms part of a bearing joint that enables said retractor blade to be altered in orientation relative said elongated element, wherein a threaded receptacle is formed in that bearing that selectively receives said connection nub.

13. The assembly according to claim 12, further including an adjustment mechanism for selectively creating a bend in said pivot joint.

* * * * *